United States Patent [19]

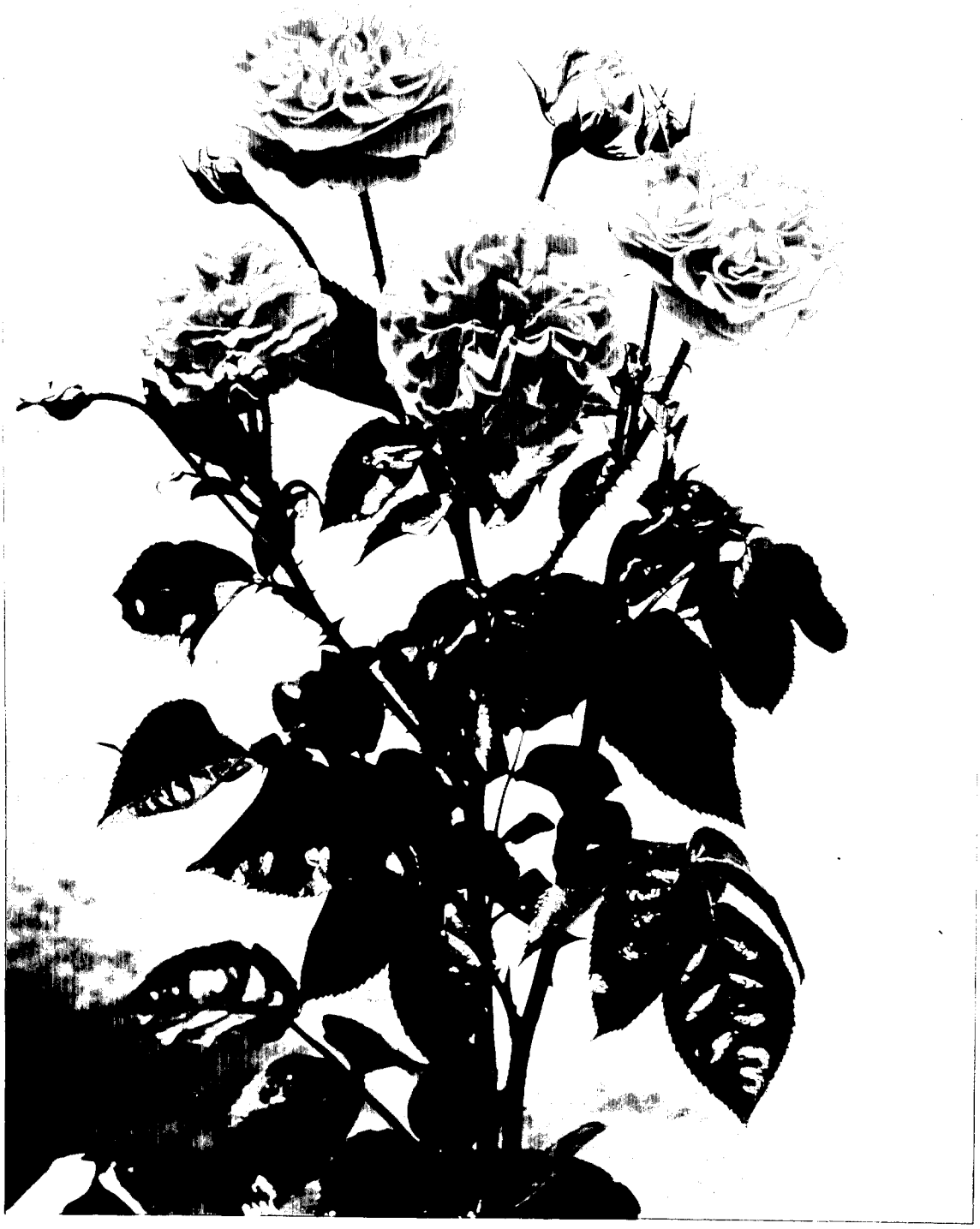

McGredy

[11] Patent Number: Plant 5,764

[45] Date of Patent: Jul. 15, 1986

[54] NEW ROSE PLANT

[76] Inventor: Samuel D. McGredy, 130 B Beach Rd., Castor Bay, Auckland 9, New Zealand

[21] Appl. No.: 625,032

[22] Filed: Jun. 27, 1984

[51] Int. Cl.[4] ..... A01H 5/00

[52] U.S. Cl. ..... Plt./25

[58] Field of Search ..... Plt./25-26

*Primary Examiner*—Robert E. Bagwill

*Attorney, Agent, or Firm*—Vincent G. Gioia

[57] ABSTRACT

A new floribunda rose variety of unusual orange flower coloring.

1 Drawing Figure

The present invention relates to a new and distinct variety of rose plant of the floribunda rose class, which was originated by my crossing as seed parent the rose known as "Mary Sumner" and the rose known as "Kapai" as pollen parent. The denomination of this variety is "Mac Ultra".

Among the novel characteristics possessed by this new variety which distinguish it from its parents and all other varieties of which I am aware are flowers of unusual orange coloring borne in small sprays. The color is believed to be a first in this range. The unusual flower color is complimented by very shiny and dense foliage giving a shrub-like appearance. Asexual reproduction by budding of the new variety as performed in Clackamas County, Oreg., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "34A" is plate 34A of The Royal Horticultural Society Colour Chart.

Parentage: Seedling.

*Seed parent.*—"Mary Sumner".

*Pollen parent.*—"Kapai".

Class: Floribunda-shrub.

The following observations are made of specimens grown outdoors in Clackamas County, Oreg., during the month of June.

1. FLOWER

Blooming habit: Continuous.

A. Bud:

(1) *Size.*—Medium.

(2) *Form.*—High centered.

(3) *Color.*—When sepals first divide — Near 34A.

(4) *Sepals.*—Longer than bud, simple, glabrous outside, wooley inside, finely serrate edge with few glandular hairs.

(5) *Peduncle.*—Length — Short, 1½ to 2 inches. Aspect — Upright. Strength — erect, with some prickles. Color — Near 181B.

Bloom:

(1) *Size.*—Average size when fully expanded — about 3 inches.

(2) *Borne.*—Several together in small sprays (clusters).

(3) *Form.*—High centered at first quickly opening into flat, tightly imbricated blooms.

(4) *Petalage.*—Number of petals under normal conditions — About 30.

(5) *Color.*—After sepals divide, bud color is near 41A becoming near 41B after sepals fall. When petals unfurl flower color remains near 41B, vermillion, lightening to azalea pink 41C. As flower opens and ages color range varies from 41B to 41D as flower color fades.

C. Petals:

(1) *Texture.*—Thick.

(2) *Appearance.*—Satiny inside and outside.

(3) *Form.*—Oval, deltoid.

(4) *Arrangement.*—Imbricate, quarters slightly before petals fall.

(5) *Petaloids in center.*—Few.

(6) *Persistence.*—Drop off cleanly.

(7) *Fragrance.*—Slight, sweet.

(8) *Lasting quality.*—Long lasting on plant and as cut flower.

2. REPRODUCTIVE ORGANS

A. Stamens, filaments and anthers:

(1) *Arrangement.*—Stamens regular, arranged and incurved.

(2) *Color.*—Near 150B.

B. Pollen:

*Color.*—Near 23A.

C. Styles: Few, even length to stamens, hairy, tightly bunched, near 10C.

D. Stigmas:

*Color.*—Near 11A.

E. Hips:

*Shape.*—Globular.

*Size.*—Small.

*Color.*—Near 32A.

*Do seeds protrude?*—No.

3. PLANT

A. Form: Tall, slightly spreading, vase-shaped.

B. Growth: Very vigorous, many blooming clusters initiated as basal canes.

*Height attained.*—About 3½ feet.

C. Foliage: Compound 5 to 7 leaflets, mostly 7.

(1) *Size.*—Medium.

(2) *Quantity.*—Abundant with short internodes.

(3) *Color.*—New foliage: Upper side — Near 178A. Under side — Near 178B . Old foliage: Upper side — Near 135A. Under side —Near 137C.

(4) *Shape.*—Long, oval, pointed.

(5) *Texture.*—Upper side is glossy and under side is dull.

(6) *Edge.*—Serrate.

(7) *Serration.*—Simple.

(8) *Leaf stem.*—Color — Near 138B. Under side — Near 144B.

(9) *Stipules.*—Medium, narrow, slightly bearded.

(10) *Resistance to disease.*—Blackspot — Excellent. Mildew — Excellent. Rust — Excellent.

D. Wood:

(1) *New wood.*—Color — Near 181B. Bark — Smooth.

(2) *Old wood.*—Color — Near 144C. Bark — Smooth.

E. Thorns:

(1) *Thorns.*—Quantity (main stalk) — Few. On laterals from stalk — Few. Form — Broad, long, slight recurve. Length — Long. Color — Near 46B. Position — Irregular.

(2) *Prickles.*—Few at base, few on laterals.

F. Winter hardiness: Needs winter protection.

I claim:

1. A new and distinct variety of rose plant of the floribunda class, substantially as shown and described, characterized particularly by unusual orange flowers borne in small clusters contrasting with attractive shiny foliage.

* * * * *